United States Patent [19]
Boberg

[11] Patent Number: 5,985,070
[45] Date of Patent: Nov. 16, 1999

[54] METHOD FOR STRETCHING A WEB OF MATERIAL IN THE MANUFACTURE OF A LIQUID ABSORBENT ARTICLE AND A DEVICE FOR STRETCHING THE WEB OF MATERIAL

[75] Inventor: Fredrik Boberg, Alingsås, Sweden

[73] Assignee: Scahygiene Product AB, Goteborg, Sweden

[21] Appl. No.: 08/849,687

[22] PCT Filed: Dec. 8, 1995

[86] PCT No.: PCT/SE95/01477

§ 371 Date: Sep. 29, 1997

§ 102(e) Date: Sep. 29, 1997

[87] PCT Pub. No.: WO96/18366

PCT Pub. Date: Jun. 20, 1996

[30] Foreign Application Priority Data

Dec. 13, 1994 [SE] Sweden .................................. 9404331

[51] Int. Cl.⁶ ............................ B32B 31/08; B29C 53/16; D06C 3/02
[52] U.S. Cl. ........................... 156/164; 156/229; 156/494; 26/52
[58] Field of Search ..................................... 156/163, 164, 156/229, 494, 495, 496; 26/51, 52; 226/93, 195

[56] References Cited

U.S. PATENT DOCUMENTS

| 1,345,634 | 7/1920 | Ryamond, Jr. ........................ 26/96 X |
| 2,397,838 | 4/1946 | Chavannes . |
| 2,434,111 | 1/1948 | Hawley, Jr. et al. . |
| 2,916,899 | 12/1959 | Hepp et al. ............................ 26/96 X |
| 3,644,157 | 2/1972 | Draper ................................ 156/164 X |
| 4,786,346 | 11/1988 | Ales et al. . |
| 5,022,336 | 6/1991 | Iwase ...................................... 26/96 X |
| 5,213,645 | 5/1993 | Nomura et al. ......................... 156/164 |

FOREIGN PATENT DOCUMENTS 0 443 244 A1  8/1991  European Pat. Off. .
0 510 715 A1  10/1992  European Pat. Off. .

*Primary Examiner*—Jeff H. Aftergut
*Assistant Examiner*—Shawn A. Mitchell
*Attorney, Agent, or Firm*—Burns, Doane, Swecker & Mathis LLP

[57] ABSTRACT

Method and device for stretching a web (8) of material in the manufacture of a liquid-absorbent article, having an absorption body (4) and a cover enclosing the same. The article is made from the web (8) of material being fed in its longitudinal direction, on which web one or more elongated elastic members (11–14) are fastened. The members extend at an angle to the longitudinal direction of the web and thereby subject the web to forces which are directed transversely to the longitudinal direction of the web. The web (8) of material is kept stretched in its longitudinal direction as well as in its transverse direction by mechanical restraint of the web of material adjacent to its longitudinal edge-portions (19,20).

5 Claims, 3 Drawing Sheets

METHOD FOR STRETCHING A WEB OF MATERIAL IN THE MANUFACTURE OF A LIQUID ABSORBENT ARTICLE AND A DEVICE FOR STRETCHING THE WEB OF MATERIAL

TECHNICAL FIELD

The present invention relates to a method and a device for stretching a web of material in the manufacture of a liquid-absorbent article. The article comprises an absorption body and a cover enclosing the same and is made by said web of material which is fed in its longitudinal direction and to which elongated elastic elements are fastened. These extend at an angle to the longitudinal direction of the web and thereby exert forces on the web. The forces are directed transversely to the longitudinal direction of the web. The web of material is kept stretched in its longitudinal direction as well as in its transverse direction by mechanical restraint of the web of material adjacent to its longitudinal edge portions. The restraint is achieved by pressing restraining members against the web of material until the web is penetrated. After the penetration, the restraining members are held in positions where they occupy holes in the web and provide support surfaces directed substantially transversely to the plane of the web. The surfaces engage portions of the web at the respective holes formed during the penetration. The stretching of the web of material is maintained during the fastening of said elastic elements.

BACKGROUND ART

From EP-A1-0 510 715 it is known as prior art to manufacture liquid-absorbent articles consisting of an absorption body and a cover, where the cover is manufactured from continuously fed webs of material. The article is formed as a diaper, an incontinence-protection, training pants or the like, in which elastics around the legs are achieved by placing and fastening elongated elastic members on one of the webs of material, wherein said elastic members have been given a continuously sinusoidal extension over the longitudinal direction of the web of material. By the extension of the elastic members and their fastening to the web of the material, said web is affected by forces pointing in different directions, i. a. transversely to the longitudinal direction of the web of material. The forces exerted on the web of material in its longitudinal direction by the elastic members are counteracted by stretching the web of material by means of feeder-rollers during the manufacture of the article. In order to counteract the forces exerted on the web of material transversely to its longitudinal direction it is known to apply a vacuum against the web of material. This however presupposes that the web of material is air-tight or only permeable to a limited degree. Thus, this method is not applicable for stretching a web of liquid-permeable material which is used as one side of the article.

U.S. Pat. No. 2,434,111 discloses a method and an apparatus of manufacturing elastic fabrics using pins as restraint means carried by chains forming part of a transportation device. As the fabric connects with the pins directly at a roll, the restraining effect in the longitudinal direction will not be fully performed with the risk that the elastic fabric will not be restrained to a smooth surface at the moment when elastic elements are fastened.

SUMMARY OF THE INVENTION

The object of the present invention is to eliminate the aforementioned inconveniences in the manufacture of absorbent articles of the aforementioned type so that the web of material is kept well stretched in every direction.

Said object is achieved by a method and a device according to the present invention restraining members extend in a continuous loop and substantially linearly over an engagement-portion of the loop. The web of material is fed over a portion linearly toward said engagement-portion at an acute, small angle to the web of material.

By the method and device according to the invention, the contracting action of the elastic members is counteracted transversely to as well as along the longitudinal direction of the web of material.

DESCRIPTION OF THE DRAWINGS

The invention will be described in greater detail below by means of an embodiment and with reference to the accompanying drawings, in which FIG. 1 diagrammatically shows an example of a device according to the invention, viewed from above.

DESCRIPTION OF A PREFERRED EMBODIMENT

Figure 1:
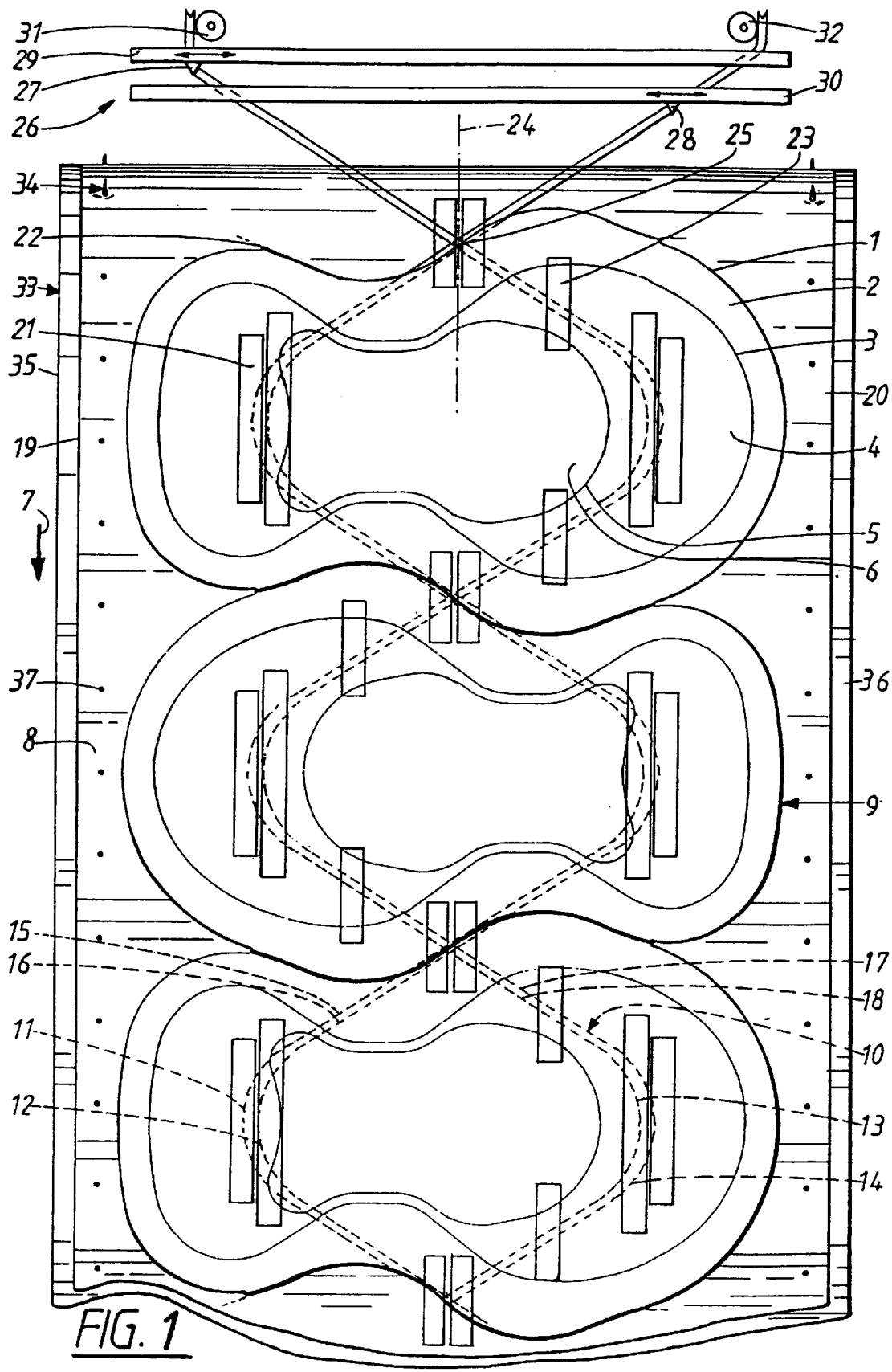

FIG. 1 shows a simplified view of the real situation, since it shows a portion of a machine for the manufacture of diapers, more precisely in the starting end of the machine, whereby, however, the appearance of virtually finished diapers is shown in the view. Thus, diagramatically, the contour-shape of the separate diapers has been shown "prematurely", namely the external contour 1 of the circumferential, flange-like edge-portion 2 of the diaper, the external contour 3 of the absorption body 4 of the diaper and the external contour 5 of the super-absorbent inner core 6 of the absorption body 4.

The diapers are arranged with their longitudinal direction arranged transverse to the longitudinal direction which is the same as the direction of feed (see arrow 7) of a web 8 of material, forming one side of a cover enclosing the absorption body. The other side of the cover is formed by a second web of material (not shown) which, after the layout of absorption bodies in a later stage of the manufacture of the diapers, is joined to the first web of material with the absorption bodies therebetween, which is not shown in the drawings.

The first web 8 of material shown in FIG. 1 may be made of either a liquid-proof or a liquid-permeable material. Examples of liquid-proof materials for this purpose are thin plastic films of polyethylene, polypropylene, polyvinylchloride or the like. Examples of liquid-permeable materials are fibre cloth (non-woven) or a soft perforated plastic film of polyethylene or the like. The absorption body 4, 6 may consist of cellulosic fibres, tissue applied by means of compressed air, different types of super-absorbent materials etc.

In order to give the diaper 9 its desired shape for its position of use, the diaper is provided with contracting elastics 10, which are arranged to have a special configuration and location. By desired shape is meant a shape, such that the diaper, in a position of use, can hold large amounts of liquid and solid excreta from the body, partly due to absorption by the absorption body and partly due to a shape-determined containment of the products, be they urine, blood or other body liquids or faeces. To this end the elastics 10 are at least partly provided with arcuately curved portions 11–14, merging into substantially rectilinear portions 15–18, at an oblique angle relative to the longitudinal direction of the web of material (see arrow 7) and thereby relative to the longitudinal edge-portions 19, 20 of the web of material.

The elastics 10 consist of longitudinal elastic members in the shape of threads or bands with a core of a highly elastic material, for example rubber, and a spun-wound thread-cover, which is connected to the web 8 of material by adhesive applied in a plurality of adhesive strands 21, 22, 23, said strands being intermittently applied on the web of material and extending in the longitudinal direction of the web of material for reasons of convenience in the production process. The application is not shown in the figures, but may be executed in a manner previously known by using a number of adhesive-nozzles for liquid adhesive, which are quickly opened and closed according to a predetermined program. In the shown example, seven such nozzles are arranged in a row transversely to the web of material.

In the shown example the elastic members are laid out in pairs over the web of material in a sinusoidal pattern. More particularly, two pairs of elastic members 11–14 are laid out in such a way, that both pairs exhibit a mutual displacement amounting to half a period of a sinus curve. Expressed in another way, it may be said that the two pairs of elastic members exhibit a pattern such that they substantially form mirror-images relative to an imaginary geometrically-longitudinal central axis 24. The curve shape of the two pairs of elastics may however differ and may have different amplitudes, but they are adapted in such a way that they substantially exhibit a common crossing 25 adjacent to the external peripheral edge-portion of the diaper. In this way, a closed area is formed by the elastic members for each separate diaper, where the elastics form an edge-barrier around a substantially closed gathering area for the excreta of the body.

The application of the elastic members is achieved in the shown example by an elastics-application device 26 which is shown purely diagrammatically in FIG. 1. The elastics-application device 26 consists of two application heads 27, 28, being reciprocatingly moveable in a linear movement transverse to the direction 7 of feed of the web 8 of material along guides 29 and 30 respectively, by means of a separately arranged driving-device for each application head. The application heads are shown, for the sake of clarity, situated a small distance from the web of material in FIG. 1, but in practice they are advantageously arranged relatively close to the web in order give the elastic members 11–14 a well-defined position. The elastic members extend in pairs through each application head from storage rolls for the elastic members (not shown). In order for the elastics to obtain contracting characteristics they are pre-stressed by means of special pre-stressing rolls 31, 32 which may be arranged in a previously known manner in order to stretch the elastic members in a longitudinal direction relative to a fully relaxed condition.

Even if the web 8 of material is supported by a conveyor 33 in the shape of a conveyor belt, the pre-stressed elastics will strive to contract the web of material in its longitudinal direction as well as in the transverse direction of the web. This could present problems, especially at the straight portions along the web of material, when absorption bodies are laid out and the second web of material is joined to the first web with the absorption bodies therebetween. To this end the machine for the manufacture of liquid-absorbent articles is provided with a device for keeping the first web of material stretched during the manufacture of the article.

The stretching device according to the invention is of a mechanical type for mechanically restraining and holding the longitudinal edges 19, 20 of the web 8 of material during at least part of the manufacturing process of the article. The stretching device 34 exhibits a plurality of restraining members 37 along the conveyor 33 adjacent to its longitudinal edges 35, 36, said restraining members 37 being arranged to engage and restrain, by a shapewise locking, the web 8 of material adjacent to its longitudinal edges 19, 20.

Figure 3:
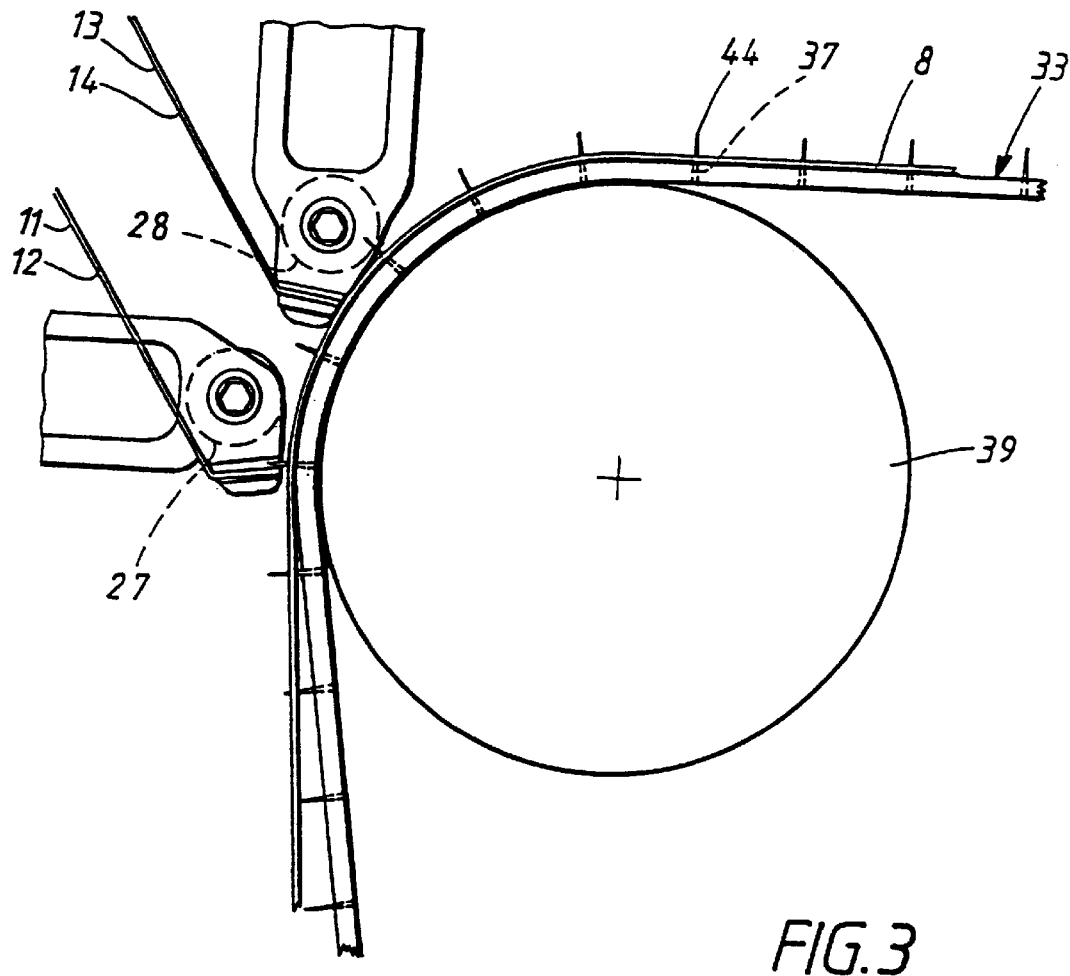
FIG. 3 shows a partial view of the invention on a larger scale, viewed from the side
Figure 4:
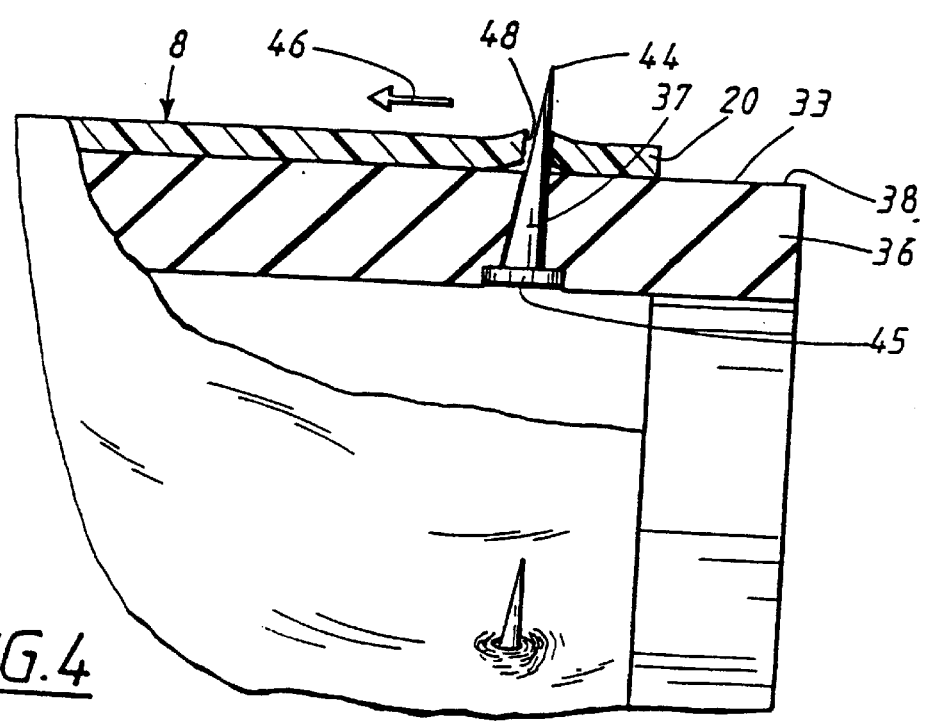
FIG. 4 shows a partially cut-away view of a portion of the device.

The chosen embodiment of the stretching device 34 will now be described with reference to all the figures. In the shown example the restraining members 37 are provided with penetration means by virtue of the fact that the restraining members are made as pegs or needles, anchored in the conveyor 33 so that they project substantially transversely to the supporting surfaces of the conveyor or conveyor belt. The conveyor belt consists of a continuous belt, made of an elastic, flexible material, and is redirected around a number of rollers 39, 40, of which two rollers are shown in the drawings. The conveyor is divided by means of the rollers into an engagement-portion 41, a feeder-portion 42 for feeding the web of material through the machine for the manufacture of the articles, and a return-portion 43 for the conveyor belt. The penetration members are, as best shown in FIGS. 3 and 4, formed as a point 44 at the free end of the restraining members. In order to obtain good anchoring the restraining members in the shown example are brought through holes in the conveyor belt and provided, on the opposite side of the supporting surface 38 of the belt, with an expanded head 45, which may advantageously be countersunk into the belt and fixedly attached to the belt by, for example, vulcanization. The restraining members 37 are advantageously made of a hard metallic material, such as stainless steel. They may advantageously be attached with a small outward inclination in the direction towards the longitudinal edge 36 of the conveyor belt whereby, in spite of the conical shape of the member, the contour-line on its "active" side, i.e. the side facing the longitudinal edge 36, will at least not have an inward inclination towards the geometrical longitudinal axis 24 of the conveyor and web of material. In this way, the risk is minimized that the supporting forces, as a result of the contracting effect of the elastics on the web 8 of material (see arrow 46) will create a lifting force-component in a direction towards the tip 44 of the restraining members with the risk of the web of material lifting off and thereby contracting.

The restraining members 37 in the shown example, are arranged in a row along each of the longitudinal edges 35, 36 of the conveyor at a distance from said edges such that the retaining members end up a certain distance inside the longitudinal edges 19, 20 of the web 8 of material and outside of the area occupied by the diaper, i.e. outside of the external contour 1 of the diaper. The restraining members may be arranged with a very large variation in mutual distances depending on the contracting effect of the elastics and the material used in the web. In principle, restraining members may be positioned anywhere along the conveyor belt outside the contour-line 1 and not necessarily in rows, but the shortest distance between the restraining members should be the same as the width of the finished article. In practice, at least one restraining member is required in alignement with each article, i.e. the diaper in the shown example, and one member in the transition between each diaper, but a separation in the order of 1–15 cm results in a homogenous restraining and stretching of the web of material.

Figure 2:
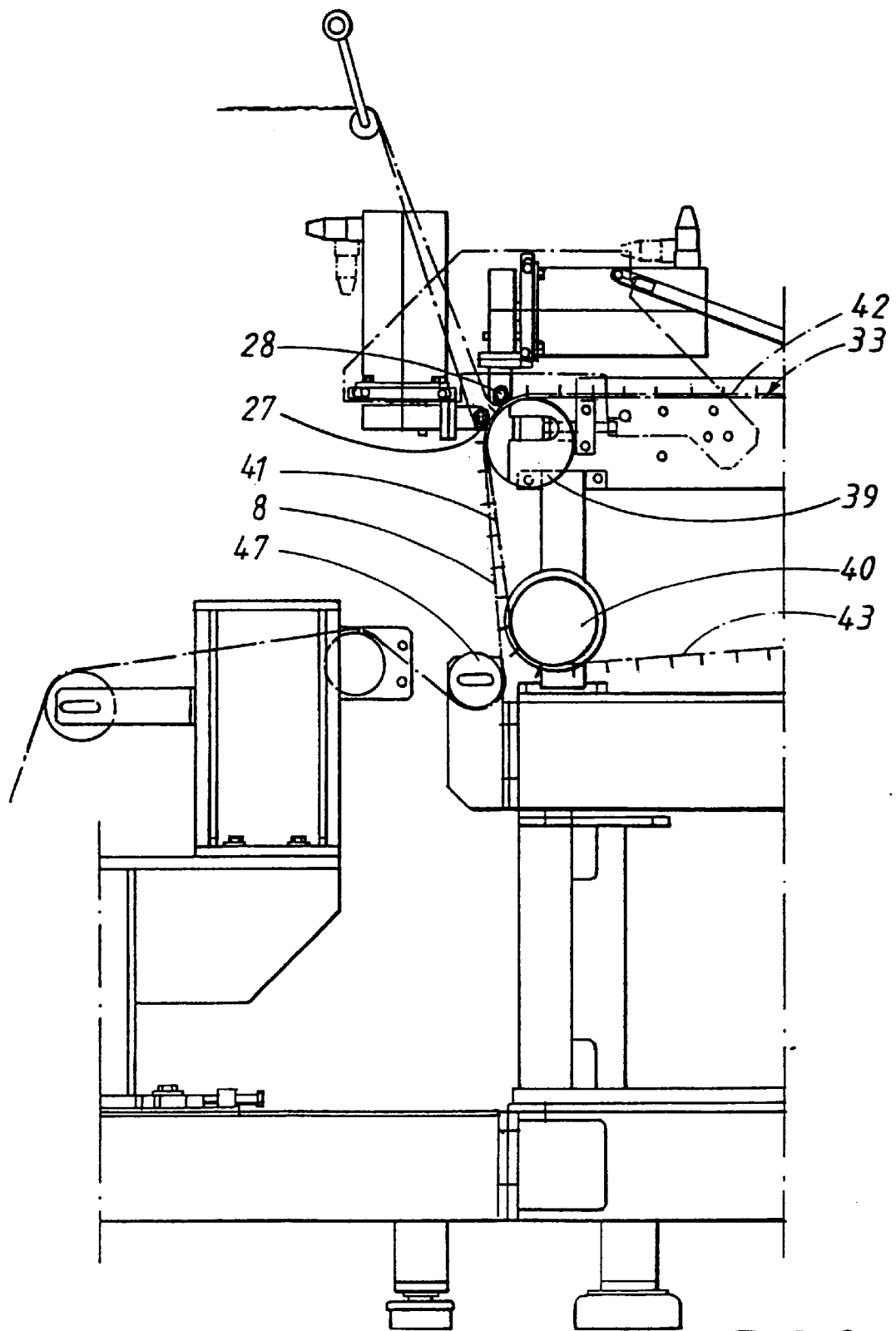
FIG. 2 shows a side-view of the device.

As is apparent from FIG. 2, the engagement-portion 41 of the conveyor 33 extends between two rollers 39, 40 around which the direction of the belt changes, i.e. over a planar portion of the conveyor's extension and not in conjunction with a point of redirection at any of the rollers. To this end, the number of rollers in the conveyor 33 is at least three, with two upper rollers (only one is shown), between which the feeder-portion extends and at least one additional roller 40 which thus forms the engagement-portion 41 together with the roller 39.

As shown in FIG. 2 a number of rollers, three in the shown example, are arranged at the starting end of the machine in order to give the web 8 of material a well adapted tension in longitudinal direction and a correct connection to the conveyor 33. The web of material is continuously unwound from a storage roll, not shown, the rotation of which is achieved by a drive-motor, the speed of which is very accurately controlled to give a correct speed and tension in the web of material in its longitudinal direction. The conveyor 43 is also driven by drive-motor, not shown, driving at least one of the rollers with an accurately adapted speed. The other rollers may also be driven synchronously with drive-motors, whilst lighter rollers may idle due to the friction between the rollers and the web of material.

As shown in FIG. 2, the roller 47 is placed in such a way, that the web of material extends towards the roller 39 and thereby the periphery of the conveyor at an acute angle v (see FIG. 3), to the conveyor belt. The angle is preferably as small as possible so that the restraining means 37 is made to penetrate the web of material in the planar portion of the conveyor, i.e. the engagement-portion 41, and thus after the conveyor has been redirected by the roller 40 and before the redirection with the roller 39 takes place. The longest penetration distance is obtained with minimal deformation, when the angle v is such that penetration is initiated directly after the redirection of the conveyor belt with the roller 40. By making the penetration occur at a small angle to the conveyor over a planar portion of the same instead of a redirection portion, the tips 44 of the restraining members will describe a movement during the penetration, as seen in the longitudinal direction, which substantially coincides with the movement of the web 8 of the material. The penetration is executed whilst the web 8 of material, over its portion between the rollers 47, 39, is held at a well adjusted tension and during feed at the same speed as the conveyor belt is made to successively close in on the restraining members 37, which are thereby pressed with their tips 44 against the surface of the web until it is punctured and a hole 48 is formed in the web of material. The restraining members 37 successively penetrate the web of material at the engagement-portion 41 of the conveyor, said web being pressed tightly against the supporting surface of the conveyor upon the redirection around the roller 39, which position is maintained in the different steps of manufacture until the completion of the diaper. In an end phase of the manufacturing process the diapers are cut out or stamped out.

As is clear from FIG. 4 a reliable restraining of the web of material is achieved by means of the restraining members 37 which stabilize the web of material in all directions and balance all forces exerted on the web of material. The restraining of the web of material to counteract the contracting effect of the elastics is effected by having the restraining members form an abutment surface against the edge-portions formed around the hole 48 of the web of material, and particularly the edge-portion on the outer side of the restraining member.

The invention is not limited to the embodiment described above and shown in the drawings, but may be varied within the scope of the appended claims. For example it is possible that the restraining members 37 exhibit a completely different shape than the conical pegs shown in the drawing. The pegs may for example be replaced by very thin needles having a homogenous cross-section or thin, leaf-like elements. It is however possible that the restraining members are made as clamping members, arranged to fixedly clamp the web of material along its longitudinal portions 29, 30.

It is of course possible to provide another type of elastic members than spun-wound rubber thread. Instead of two pairs of elastic members the elastics may be made of a single thread.

I claim:

1. A method of restraining a web of material in the manufacture of a liquid-absorbent article having an absorption body and a cover enclosing the same, which article is made at least by said web of material which is fed in its longitudinal direction and to which one or more elongated elastic elements are fastened, which extend at least partly at an angle to the longitudinal direction of the web and thereby exert forces on the web which forces are directed transversely to the longitudinal direction of the web, the method comprising the steps of:

stretching the web of material in its longitudinal direction, extending a plurality of restraining members in a continuous loop which loop includes a substantially linear portion in an engagement portion of the loop, feeding the web of material so that the restraining members penetrate a substantially linear portion of the web while said web is being fed at a small angle against the substantially linear portion of the loop, after the penetration, holding said restraining members in positions where they occupy holes in the web and provide support surfaces directed substantially transversely to the plane of the web, said support surfaces engaging portions of the web at the respective holes formed during the penetration, said web being pressed against said support surfaces of said loop by redirecting the web about a downstream roller of the engagement portion of the loop, and maintaining said stretching and restraint of the web of material at least during the fastening of said elastic elements to the web of material.

2. A device for restraining a web of material in a machine for the manufacture of a liquid-absorbent article having an absorption body and a cover enclosing the same, which article is made at least by said web of material which is fed in its longitudinal direction and to which one or more elastic elements are fastened, which extend at least partly at an angle to the longitudinal direction of the web and thereby subject the web to forces which are directed transversely to the longitudinal direction of the web, the device comprising:

a plurality of restraining members being arranged to move through at least part of the machine with a same speed as said web of material and mechanically restrain and hold said web adjacent to its longitudinal edge-portions, the restraining members being provided with penetration means for penetrating the web of material before the elastic members are applied, said restraining members, in the restraining condition, being directed substantially perpendicularly to a main plane of the web of material, whereby a portion of each restraining member forms an abutment against an edge-portion of a hole in the web of material, said hole being formed during the penetration, a conveyor including a continuous belt and at least three rollers around which the belt is supported and which changes a direction of the belt so as to define a substantially linear engagement portion of the continuous belt for the web of material, said continuous belt being driven by a driving device and is arranged to support the web of material on a feeder portion of the continuous belt and feed the same through part of the machine in a selected direction of feed, the restraining members projecting from a supporting surface of the conveyor, the engagement-portion of the continuous belt is formed between two of said rollers before said feeder-portion, as seen in the direction of feed, and a roller for the web of material is arranged to keep a substantially linear portion of the web under tension, by cooperation with one of said rollers for the conveyor belt, to feed the web at a small acute angle against the engagement portion of the conveyor belt, said web being pressed against said supporting surface of said continuous belt upon redirection of said web around a downstream roller of said engagement-portion of said continuous belt.

3. The device according to claim 2, wherein said restraining members are arranged in at least one row along each of the two longitudinal edge-portions of the conveyor belt.

4. The device according to claim 3, wherein the conveyor belt is made of a highly flexible material and that the restraining members extend through the belt from its opposite surface relative to the supporting surface.

5. The device according to claim 4, wherein said restraining members have a needle-like shape.

* * * * *

UNITED STATES PATENT AND TRADEMARK OFFICE
CERTIFICATE OF CORRECTION

PATENT NO. : 5,985,070
DATED : November 16, 1999
INVENTOR(S) : Fredrik BOBERG

It is certified that error appears in the above-identified patent and that said Letters Patent is hereby corrected as shown below:

On the title page, item [73], Assignee: "Scahygiene Product" should read – SCA Hygiene Products--.

Signed and Sealed this

Twenty-seventh Day of March, 2001

Attest:

NICHOLAS P. GODICI

Attesting Officer     *Acting Director of the United States Patent and Trademark Office*